United States Patent [19]

Bessis

[11] 4,428,669
[45] Jan. 31, 1984

[54] METHOD AND DEVICE FOR MEASURING THE DEFORMABILITY OF LIVING CELLS, NOTABLY OF RED BLOOD CORPUSLES

[75] Inventor: Marcel Bessis, Paris, France

[73] Assignee: Institut Nationale de la Sante et de la Recherche Medicale, Paris, France

[21] Appl. No.: 269,252

[22] Filed: Jun. 1, 1981

[30] Foreign Application Priority Data

Jun. 6, 1980 [FR] France .................................. 80 12592

[51] Int. Cl.$^3$ ........................................... G01N 33/48
[52] U.S. Cl. ..................................................... 356/39
[58] Field of Search ........................................... 356/39

[56] References Cited

U.S. PATENT DOCUMENTS

| | | | |
|---|---|---|---|
| 3,413,464 | 11/1968 | Kamentsky | 356/39 |
| 3,822,095 | 7/1974 | Hirschfeld | |
| 3,873,204 | 3/1975 | Friedman et al. | |
| 3,947,123 | 3/1976 | Carlson et al. | 356/39 |
| 3,955,890 | 5/1976 | Bessis et al. | |
| 4,209,256 | 6/1980 | Faulkner | 356/39 |
| 4,338,024 | 7/1982 | Bolz et al. | 356/39 |
| 4,352,558 | 10/1982 | Eisert | 356/39 |

FOREIGN PATENT DOCUMENTS

| | | | |
|---|---|---|---|
| 2201524 | 7/1973 | Fed. Rep. of Germany | 356/39 |
| 2121987 | 8/1972 | France | |
| 2405839 | 8/1975 | Fed. Rep. of Germany | |

Primary Examiner—Vincent P. McGraw
Attorney, Agent, or Firm—Cushman, Darby & Cushman

[57] ABSTRACT

In order to produce easily a deformation in a cell population enabling the production of an optical diffraction pattern, a liquid containing a suspension, either homogeneous, or localized, is passed into a transparent tubular channel with a fixed wall in the form of a laminar flow, the beam passing through this channel perpendicularly. This method avoids the use of movable mechanical means for obtaining the conditions necessary for the deformation of the cells, and permits valuable indications to be obtained on the quality of the hemoglobin and the structure of the wall.

15 Claims, 4 Drawing Figures

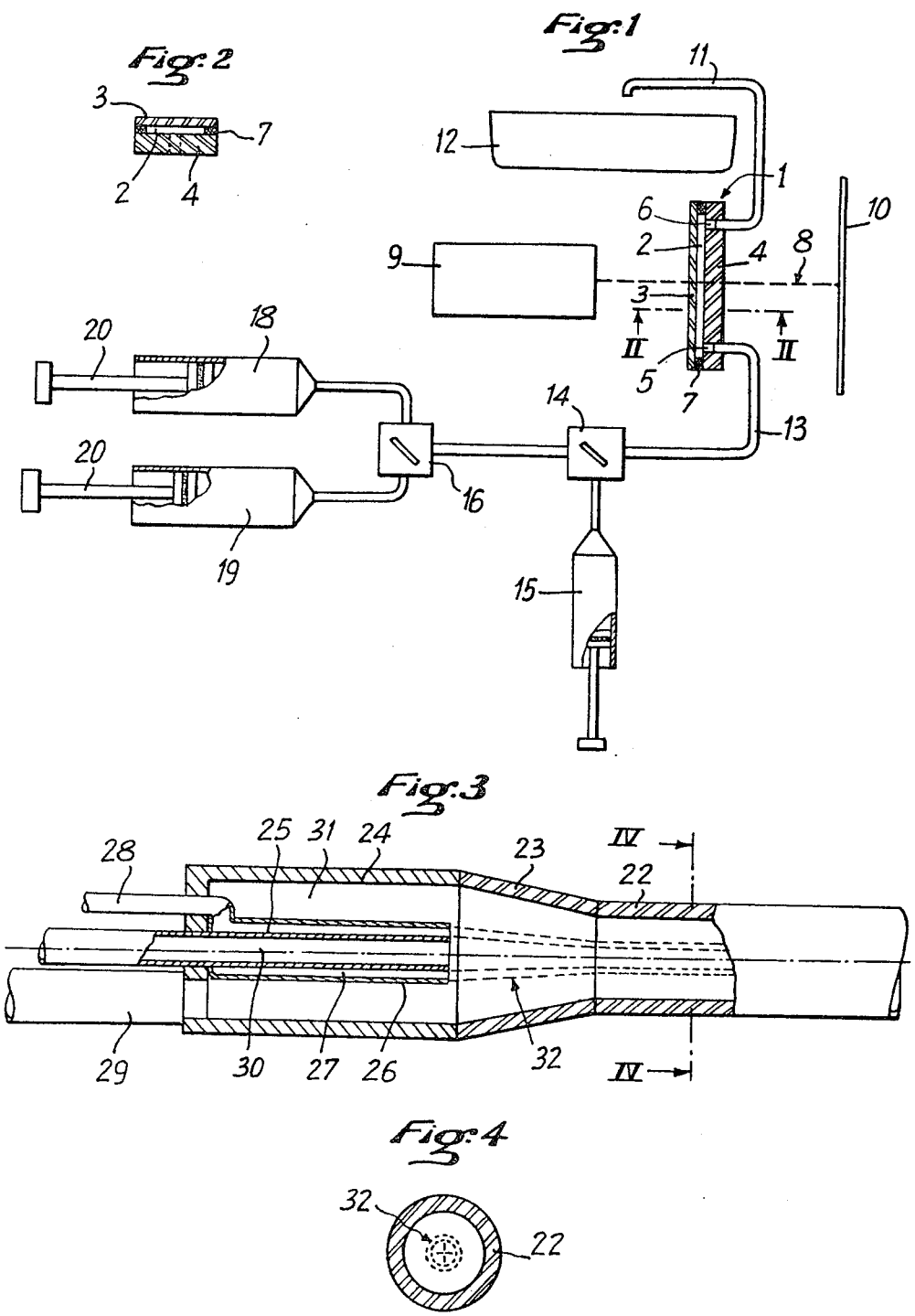

METHOD AND DEVICE FOR MEASURING THE DEFORMABILITY OF LIVING CELLS, NOTABLY OF RED BLOOD CORPUSLES

BACKGROUND OF THE INVENTION

1. Field of the Invention

The present invention relates to a method and to a device for measuring the deformation capacity of living cells, such as red blood corpusles.

It is known that the capacity of deformation of red cells plays an essential role in their functions and their life span and constitutes a valuable indication relating the quality of the hemoglobin, the structure of the wall and other characteristics, so that the measurement of this deformation capacity is now used for exploration and diagnosis of different disorders, notably hematological.

2. Description of the Prior Art

Numerous techniques have already been proposed to measure the deformation capacity of red blood corpusles. A particularly accurate and practical method is to be found in French Pat. No. 74 16160 published under No. 2,270,557 and consisting of placing a liquid containing red blood corpuscles in suspension between two transparent coaxial walls and communicating to these two walls different rotary speed, with respect to their common axis, causing a parallel beam of light to pass through the liquid, substantially normal to this common axis, to obtain a diffraction pattern on which the characteristic dimensions of the diffraction rings as a function of the differential speed of the two walls, are measured.

In fact, the speed of flow gradient caused by the difference of rotary speeds ensures, through the corresponding shearing effect, a good deformation of the whole of the suspended cell population passing between the walls.

This method, if it gives entire satisfaction, necessitates however the use of a relatively complex device with two coaxial cylindrical walls movable in rotation with respect to one another, means for imparting to these walls different rotary speeds with respect to their common axis and means for directing a light beam, notably of coherent monochromatic light, perpendicularly to the common axis through the flow thus generated.

It is an object of the present invention to provide a method for measuring the capacity of deformation of living cells such as red blood corpuscles, which is easy to put into operation and not laborious, whilst providing measurement results which can achieve very high accuracy.

Another object of the invention is to provide a method which enables very easily, exploration by variation of one or several of the parameters of the medium containing said bodies, and notably the red blood corpuscles.

Another object of the invention is to provide a particularly simple, economic and reliable device for measuring the deformation capacity of microscopic bodies, and notably of living cells such as red blood corpuscles, enabling easy practising of the aforesaid method.

GENERAL DESCRIPTION OF THE INVENTION

According to the invention there is provided a method for measuring the capacity of deformation of living cells such as red blood corpuscles, in suspension in a liquid through which a parallel beam of light is passed to observe the diffraction pattern produced by the cells in order to measure the characteristic dimensions of the diffraction rings, characterised by the fact that the suspension contained in this liquid is caused to pass into a tubular channel with a fixed wall in a direction substantially perpendicular to said beam in the form of a flow which is laminar or close to the laminar condition, the beam passing through the suspension in this channel.

The invention rests on the surprising discovery that in causing the liquid suspension to pass at a sufficient speed through the channel, without other precaution, a diffraction pattern is obtained whose quality is sufficient to permit accurate measurements, in spite of the fact that in a large part of the passage cross-section of the flow, the speed gradient which determines shearing is nil or not substantial.

According to the invention, through said channel a flow which is laminar or close to the laminar condition, of this liquid, is produced.

According to a first simplified embodiment of the invention, a suspension of the cells is prepared in a suitable liquid, gaving the desired characteristics of tonicity and viscosity, and this liquid is lead to pass, in the form of a flow which is laminar or close to the laminar state, through the channel, said channel having a sufficient length to permit the establishment and/or preservation of this state in a zone traversed by the light beam, preferably a coherent monochromatic light beam.

Preferably, the passage cross-section of the channel is greater than 0.0005 mm$^2$ and the liquid flow rate through the cross-section is greater than 0.1 ml/min.

According to an improvement of the invention, it is possible advantageously to gradually modify, during the measurement, one or several of the characteristics of the medium, for example the partial pressure of oxygen or carbon dioxide, the viscosity, the tonicity, etc. . . . , without being bothered by the need, as in the prior art, of passing a continuous flow through a device actuated by rotary movements.

In a second embodiment of the invention, enabling measurements to be carried out with a particularly high degree of accuracy, it is possible to conduct the liquid, devoid of cells, to flow through the channel and into the liquid, at the level of the channel and at a place of the passage cross-section both spaced from the center of this section and from the wall of the channel can be injected a flow of cells, such as red blood cells, in a direction neighboring or identical with the direction of flow of the liquid, so that said cells pass through the path of the light beam by being contained in this portion of the passage cross-section.

In this embodiment also, it is possible advantageously to vary progressively the characteristics of the medium in which the red blood cells are present, either by modifying the characteristics of said liquid, or by modifying the characteristics of the medium transferring the cells to the injection site.

The passage cross-section in the channel can have any desired shape, notably square, rectangular or circular. Preferably, the separation between two opposite points of the wall, in the direction of the light beam, is greater than 25$\mu$, for example from 100 to 150$\mu$.

In the case wherein the cells are injected into the liquid flow through the channel, the injection can be effected either at one or several different points, or in a continuous section portion, preferably annular. Thus, in the case of a channel with a circular cross-section, the injection can be effected in a part of annular or circular cross-section; for example for a channel diameter of 100μ, the thickness in the ring can be about 25μ.

According to another aspect of the invention there is provided a device for practicing this method, which device is characterised by the fact that it comprises a channel with a transparent wall of sufficient length to permit the establishment for the maintenance of a flow of liquid which is laminar or close to the laminar state, the entrance of said channel being connected to means permitting the introduction of a liquid under sufficient pressure to establish said flow, said device comprising on the other hand, means for causing to pass through said channel, and in a direction substantially perpendicular to the direction of flow, a light beam, preferably of coherent monochromatic light, designed to provide a diffraction image.

The means for introducing liquid can advantageously comprise at least one pump connected to the channel so as to ensure a flow of liquid to and through the channel.

In a first embodiment of the invention, the device may advantageously include means for producing, upstream of said channel, a suspension of said cells in the liquid, for example by providing in the path of the liquid to the channel, an injection zone so as to produce a homogeneous suspension intended to flow through the channel.

The device can however also be without these means, the suspension being formed outside of the device, and then introduced already fully prepared into the latter.

On the other hand, in a second embodiment, the device may advantageously include, at the level of the channel, means for the introduction of a flow of cells into a portion of the cross-section of the channel spaced for example from the channel or from its wall, and this in a direction substantially parallel to the direction of flow.

Particularly advantageously, these injection means can comprise one or several needles oriented in the direction of flow and opening at the desired level of the cross-section of the channel.

Preferably, the needle can be a needle of annular cross-section enabling the establishment of an annular flow of living cells, essenthe central portion of the needle containing a passage through which a portion of fluid devoid of cells can be passed, and designed to form the central portion of the flow.

In the case where it is desired to cause continuous variation of one or several of the characteristics of the liquid medium, the device can advantageously comprise at least two pumps terminating in a mixing chamber, the actuation, the speed of the pumps, on the one hand, and the regulation of the mixing chamber, on the other hand, being such that the progressive modification of the medium is produced according to a pre-established program.

BRIEF DESCRIPTION OF THE DRAWINGS

Other advantages and characteristics of the invention will appear from reading the description which follows, given purely by way of non-limiting example, of preferred embodiments of the invention, with reference to the accompanying drawing in which:

FIG. 1 shows a diagrammatic view of a measuring device for the capacity of deformation of red blood corpuscles according to a first embodiment of the invention.

FIG. 2 shows a view in cross-section of the channel of the device in FIG. 1.

FIG. 3 shows a diagrammatic view of the injection means and of the initial portion of the channel of a measuring device of the capacity of deformation of red blood corpuscles according to a second embodiment of the invention.

FIG. 4 shows a cross-section view of the embodiment of FIG. 3.

DESCRIPTION OF PREFERRED EMBODIMENTS

Referring now to FIGS. 1 and 2, the measuring device for the deformation of red blood cells illustrated includes a measuring channel denoted as a whole by 1 and having a port or channel proper whose passage cross-section, shown in FIG. 2, is that of a flattened rectangle of width equal to 1 cm and height equal to 100μ. The channel is formed from an upper glass plate 3 of rectangular shape and a lower thicker glass plate 4 also of rectangular shape, provided at its front and rear ends with an inlet passage 5 and an outlet passage 6. A fluid-tight peripheral seal 7 is interposed between the two glass plates 3, 4, so as to form lateral edges of the passage cross-section.

As can be seen in FIG. 1, the channel 1, whose length is about 4 cm is arranged vertically so as to be traversed by the beam 8 of a laser 9, said beam 8 being directed perpendicularly to the assembly of glass plates 3, 4 to be recovered on a screen 10 or other device enabling analysis of the diffraction image formed.

The discharge passage 6 of the channel 1 is connected by a tube 11 to a discharge receiver 12.

At its side, the inlet passage 5 is connected to an inlet tube 13 ending at a mixing chamber 14 at which terminates a pump 15, for instance a piston pump constructed in the form of a syringe and provided with actuating means (not shown), said pump 15 enabling injection with a regular flow rate, or red blood cells, into the chamber 14. The chamber 14 is on the other hand connected to a mixing chamber 16 at which end the outlets of two pumps 18 19, also shown in the form of syringes, the pistons 20 of said pumps being also driven by suitable drive means.

The liquids contained in the pumps 18 and 19 and which are mixed in the desired proportions in the chamber 16, form by mixing in said chamber the liquid intended to comprise the cell suspension. This liquid is, for example a dextran solution having the viscosity of 10 cp and the desired tonicity. Due to the use of the two pumps 18, 19 and of the mixing chamber 16, it is possible to vary, as desired, the viscosity, the tonicity or the partial pressures or again other parameters of the medium, and this so as to obtain either a medium of constant composition during the whole measurement or a medium of gradually variable composition.

In operation, it is understood therefore that the device enables the establishment through the channel proper 2 of a laminar flow of a homogeneous suspension of red blood cells in the liquid of composition provided in advance. The movement of this suspension through the channel produces a diffraction image recovered on the screen 10. This diffraction image, which has circular concentric rings when the liquid is at rest, becomes elongated and takes on a characteristic configuration when the liquid flows with a laminar movement through the channel 2, the configuration of the image being characteristic of the deformation undergone by the suspended red blood corpusles.

The flow rate of the stream traversing the channel 2, and consequently the amplitude of the flow speeds, is determined by the amount of the pressure upstream provided by the different pumps. It is also possible to provide regulating means for this flow rate in order to obtain a perfectly constant flow rate which can be established at adjustable desired values.

The various characteristics of the suspension, namely the composition of the liquid, its partial pressures, its tonicity, as well as the density of the red blood cells in the liquid, are easily defined by the technician skilled in the art and have no need to be modified with respect to the values used for measurements in equipment of the prior art such as that described in the aforesaid French Patent.

Instead of being of flattened rectangular shape, the cross-section of the channel could also be square, for example a square of $150\mu$ side, or even circular, for example of diameter comprised between 25 and $100\mu$, the length of the channel being such that taking into account the possible turbulence caused by the arrangement of liquid inlets and outlets, the zone traversed by the light beam is traversed by a flow of laminar type. In general, a length of some centimeters is sufficient.

Reference is now made to FIGS. 3 and 4.

In this second embodiment, the channel is formed inside a glass tube 22 of internal diameter $150\mu$.

This glass tube is connected to a flared portion 23 of funnel shape whose diameter decreases progressively toward the tube 22 and whose end of largest diameter is connected to a cylindrical chamber 24. Inside this chamber 24, and concentrically with the common axis of the assembly, is arranged an annular needle, that is to say, a needle having a cylindrical outer peripheral wall 26 and an inner peripheral wall 25 defining between then a narrow annular space 27 open through its front end, closed at its rear end and receiving in the vicinity of the latter an inflow of red blood cells 28 in concentrated suspension in a suitable liquid medium.

The inner wall 25 is extended outside of the chamber 24 at its rear end, and is connected to a liquid inlet tube. The same liquid is also introduced into the chamber 24 through a passage 29, the flow rates of liquid through the inner space 30 of the wall 25 and through the peripheral space 31 of the chamber 24 being such that any notable turbulence does not tend to be produced at the level of the front end of the needle 24, 25 so as to create in the vicinity of the front end of the needle a practically laminar flow zone, this laminar flow continuing inside the tube 22.

For the measurement, there is therefore established in the space 30 and in the space 31 a flow rate of liquid devoid of red blood cells so as to tend to cause in the frustoconic portion 23 and the tube 22 a flow of laminar nature and there is established simultaneously a flow of red blood cells through the annular space 27 which then forms in the liquid an annular suspension 32 of red blood cells spaced both from the axis of the tube 22 and from the wall of the latter. As is seen notably in FIG. 4, the red blood cells remain concentrated in this annular portion 32 of the cross-section in which the speed gradient is large. In this way there is obtained on the screen a diffraction image which is still more distinct and precise enabling measurements of very great accuracy.

Of course, the injection of red blood corpuscles into a suitable portion of the passage cross-section of the channel can be effected along different geometries.

Thus, in the example of FIG. 1, it would be possible, instead of injecting the red blood cells into a mixing chamber upstream of the channel 2 so as to obtain a homogeneous suspension, to inject on the contrary the red blood cells inside a chamber 1, into the channel, so the cells become disposed along a flat configuration of little thickness arranged for example at mid-distance between the inner wall of the upper glass plate 3 and the central portion of the channels 2.

It is self-evident that the technician skilled in the art could vary, not only the geometry of the cross-section of the channel, but also the dimensions of the latter as well as the value of the suspension flow rate passing through the channel. The corresponding values can be obtained by simple experiments, it being understood that the thickness of the channel, that is to say the distance traversed by the beam inside the channel, must vary as a function of the state of dilution that it is desired to obtain, as is otherwise known.

The distance traversed by the beam in the solution actually containing the erythrocytes is at least equal to $25\mu$. The upper value of this distance is preferably limited to $150\mu$, this being principally to avoid flow rates which are too high, a dilution which is too great, as well as the difficulties of maintaining a laminar flow in too large a passage cross-section, but it is self-evident that these values, indicated for practical reasons, are not critical from the theoretical point of view.

The dilution is preferably such that about 80 to 90% of the cross-section of the light beam is intercepted by the particles.

Lastly, the embodiments of the invention which have been described in detail are simply preferred embodiments and it is self-evident that the method can be put into practice by other means.

Thus, it was observable, surprisingly, that it was possible to practise the method according to the invention in devices such as those of the aforementioned French Patent, provided that the rotary walls of the latter were immobilized and that the liquid was forced to flow with the desired flow rate through the device.

The channel can be curvilinear as well as rectilinear. Although the invention has been described with regard to a particular embodiment, it is understood that it is in no way limited thereto and that it is possible to introduce various modifications of form therein without however departing from either its scope, or its spirit.

I claim:

1. A method for measuring the deformation capacity of living cells such as red blood corpuscles, suspended in a liquid through which a parallel beam of light is passed to observe the diffraction pattern reproduced by the cells in order to measure the characteristic dimensions of the diffraction rings, said method comprising the steps of: passing the suspension contained in the liquid into a tubular channel with a fixed wall and having a constant cross section, in a direction substantially perpendicular to said beam; adapting said suspension into the form of a flow which is laminar or close to the laminar state, in a location in said channel where at least a part of said flow is submitted to substantial shearing forces to effect cell deformation; and passing said beam through said suspension in said channel.

2. Method according to claim 1, comprising forming a homogeneous suspension of said cells in the liquid and bringing said liquid to pass in the form of a laminar or almost laminar flow through said channel.

3. Method according to claim 1, comprising the further steps of: causing the liquid, devoid of cells, to flow through the channel; and injecting into the liquid, at the level of the channel, at a place of limited surface of the passage section, a flow of cells in a direction neighboring or identical to the direction of flow of the liquid so that said cells form a cell suspension which passes across the path of the light beam in being contained within this portion of the passage section.

4. Method according to claim 3, wherein said injection is effected in a passage section portion of annular shape.

5. Method according to any one of claims 1 to 4, wherein the passage cross-section of the channel is greater than 0.0005 mm$^2$.

6. Method according to any one of claims 1 to 4, wherein the liquid flow rate through the channel is higher than 0.1 ml/min.

7. Method according to any one of claims 1 or 4, wherein the thickness of the solution actually containing cells and traversed by the light beam is greater than 25μ.

8. Method according to any one of claims 1 to 4, comprising gradually modifying, during the measurement, one or several of the characteristics of the liquid medium.

9. A device for measuring the deformation capacity of living cells, such as red blood corpuscles, comprising:
   a channel with a transparent wall and having a constant cross section, of sufficient length to establish or maintain a liquid flow which is laminar or close to the laminar state;
   means for enabling the introduction into the entrance of said channel liquid under sufficient pressure to establish said liquid flow;
   means for subjecting a cell suspension in at least a part of said flow to substantial shearing forces to achieve cell deformation; and
   means for passing through said channel, and in a direction substantially perpendicular to the direction of said flow, a light beam for providing a diffraction image.

10. Device according to claim 9, comprising means for forming, upstream of said channel, a homogeneous suspension of said cells to the liquid.

11. Device according to claim 9, comprising, at the level of the channel, means for the introduction of a flow of cells into a portion of limited surface of the cross-section of the channel, this being in a direction substantially parallel to the direction of flow.

12. Device according to claim 11, wherein said introduction means comprise an annular needle oriented in the direction of flow and opening into the channel section.

13. Device according to any one of claims 9 or 10–12, wherein said channel has a square or rectangular cross-section.

14. Device according to any one of claims 9 or 10–12, wherein said channel has a circular cross-section.

15. Device according to any one of claims 9 or 10–12, comprising means for gradually modifying one at least of the parameters of the suspension during the measurement.

* * * * *